United States Patent [19]

Pebler et al.

[11] 4,134,818
[45] Jan. 16, 1979

[54] SOLID ELECTROLYTE SENSOR FOR MONITORING COMBUSTIBLES IN AN OXYGEN CONTAINING ENVIRONMENT

[75] Inventors: Alfred R. Pebler, Penn Hills; Donald W. Beckett, Wilkinsburg, both of Pa.

[73] Assignee: Westinghouse Electric Corp., Pittsburgh, Pa.

[21] Appl. No.: 785,378

[22] Filed: Apr. 7, 1977

[51] Int. Cl.$^2$ ............................................. G01N 27/46
[52] U.S. Cl. ................................. 204/195 S; 204/1 T; 23/232 E; 422/98
[58] Field of Search ................ 204/1 S, 195 S, 195 R; 23/232 E, 254 E, 255 E

[56] References Cited

U.S. PATENT DOCUMENTS

| Re. 28,792 | 4/1976 | Ruka | 204/195 S |
|---|---|---|---|
| 1,940,513 | 12/1933 | Stein | 23/232 E |
| 2,349,250 | 5/1944 | Doan | 23/232 E |
| 3,296,113 | 1/1967 | Hansen | 204/195 R |
| 3,455,807 | 7/1969 | Jacobson et al. | 204/195 R |
| 3,479,257 | 11/1969 | Shaver | 204/195 R |
| 3,558,280 | 1/1971 | Panson et al. | 204/195 S |
| 3,687,631 | 8/1972 | Zegel | 23/232 E |
| 3,691,023 | 9/1972 | Ruka et al. | 204/195 S |
| 3,791,936 | 2/1974 | Pebler et al. | 204/195 S |
| 3,981,785 | 9/1976 | Sandler | 204/195 S |
| 4,005,001 | 1/1977 | Pebler | 204/195 S |
| 4,045,300 | 8/1977 | Renet | 204/1 S |

*Primary Examiner*—T. Tung
*Attorney, Agent, or Firm*—M. P. Lynch

[57] ABSTRACT

A high temperature solid electrolyte electrochemical cell is operated as a combustibles sensor in an oxygen containing atmosphere. The electrodes of the solid electrolyte electrochemical cell consist of a catalytic material such as platinum. The resistance of the solid electroltye electrochemical cell is such that it changes exponentially with inverse absolute temperature. When subjected to an oxygen/fuel environment, combustion occurs at the catalytic electrodes resulting in a temperature increase at the solid electrolyte electrochemical cell which results in a significant resistance change. This resistance change is monitored as an indication of the fuel or combustible content of the oxygen/fuel environment.

2 Claims, 5 Drawing Figures

SOLID ELECTROLYTE SENSOR FOR MONITORING COMBUSTIBLES IN AN OXYGEN CONTAINING ENVIRONMENT

BACKGROUND OF THE INVENTION

Conventional combustion meters typically employ a temperature sensor for monitoring the heat affect from the catalytic-heterogeneous combustion of fuels with excess oxygen. Most commonly used is the hot wire technique, which employs a resistance heated noble metal filament usually made of platinum. If filament is heated in an atmosphere containing fuels and sufficient oxygen for combustion, the combustion is catalyzed at the metal-interface. The heat release by the combustion raises the temperature of the wire filament thereby increasing the resistance. The wire filament typically serves as a branch in a bridge circuit. The conventional hot wire detector exhibits relatively low sensitivity which limits its usefulness for monitoring low fuel concentrations, i.e., less than 1%.

An improvement in the conventional hot wire detector can be realized through the use of commercially available thermistors. Commercially available thermistors however have suffered from the limited stability of the semiconductor material at high temperatures in an oxidizing environment, typically having a maximum operating temperature of 300° C. This temperature is less than temperatures required for combustion of methane and other hydrocarbon fuels even in the presence of catalysts.

The following description in connection with the accompanying drawings describes a solid electrode electrochemical cell functioning as the combustibles sensor suitable for operation at a temperature range of about 500° C to 1000° C in the presence of oxidizing gases.

SUMMARY OF THE INVENTION

A combustible sensor is disclosed herein consisting of a high temperature solid electrolyte electrochemical cell which acts as a catalyst for the combustion of fuels in an oxygen environment and a temperature sensor for monitoring temperature increases resulting from the catalytic combustion. A solid electrolyte electrochemical cell employs a solid electrolyte material, such as calcia stabilized zirconia, which is known to conduct electrical current at elevated temperatures on the basis of a vacancy mechanism involving doubly charged oxygen ions. The rapid change in cell resistance due to temperature changes is monitored as a change in cell current which in turn is interpreted as an indication of the combustibles content of the monitored gas. Suitable oxygen ion conductive solid electrolyte materials are described in detail in U.S. Pat. Re. No. 28,792, assigned to the assignee of the present invention and incorporated herein by reference.

DESCRIPTION OF THE DRAWING

The invention will become more readily apparent from the following exemplary description in connection with the accompanying drawings.

DESCRIPTION OF THE PREFERRED EMBODIMENT

Figure 1:
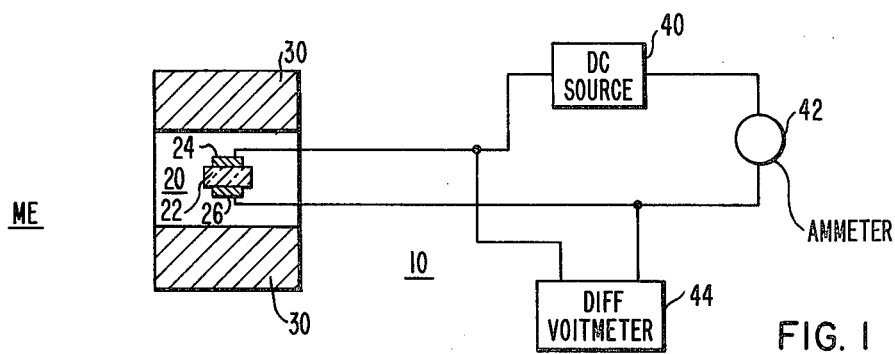
FIG. 1 is a schematic illustration of a combustible sensor employing the invention.

Referring to FIG. 1 there is schematically illustrated a combustible sensing apparatus 10 including a sensor cell 20 which responds to the combustibles excess oxygen monitored gas environment ME by developing an output current signal indicative of the combustibles content of the monitored gas environment ME.

The sensor cell 20, which consists of an oxygen ion conductive solid electrolyte 22 and catalytic electrodes 24 and 26 disposed on opposite surfaces thereof, is positioned within a furnace 30. A suitable solid electrolyte material includes calcia stabilized zirconia, as discussed in the above-referenced U.S. Patent, while the catalytic electrodes can typically consist of platinum electrodes. Other suitable electrode materials include the noble metals such as Pd and Rd.

Figure 2:
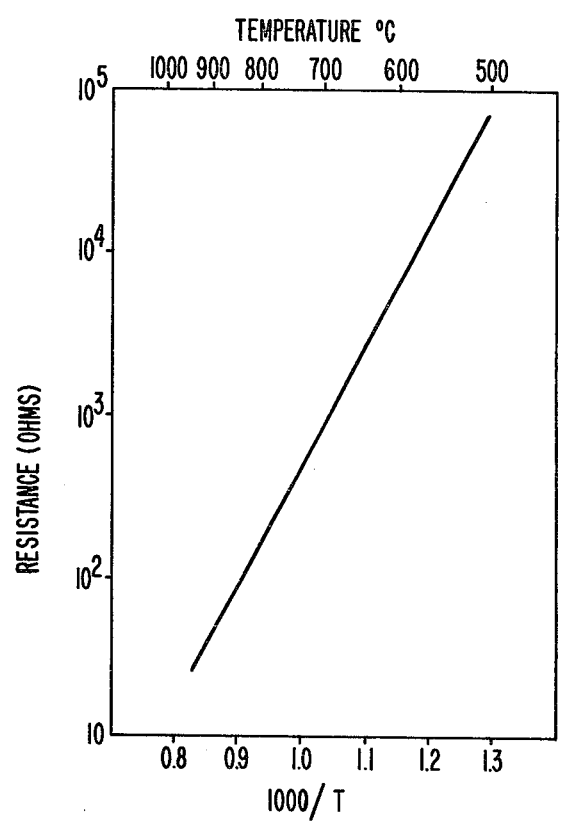
FIG. 2 is a graphical illustration of the resistance v. temperature response of the solid electrolyte sensor.

Experimental evaluation of the sensor cell 20 consisting of an oxygen ion solid electrolyte material and catalytic electrodes indicates a negative temperature coefficient, comparable to that of a conventional thermistor. A typical resistance-temperature plot of the sensor cell 20 is illustrated in FIG. 2. The resistance-temperature characteristic of the sensor cell 20, as illustrated in FIG. 2, supports the practical application of the sensor cell 20 as a combustible sensor in a combustible-oxygen gas environment wherein the oxygen present is in excess of that required for stoichiometric combustion.

In the embodiment of FIG. 1, a potential is applied across the sensor cell 20 at the electrodes 24 and 26 by the variable DC power source 40. The magnitude of the applied potential is established such that the cell current, as measured by ammeter 42, in response to variation in the resistance characteristic of the sensor cell 20 due to temperature changes, is sufficiently low so as to avoid any appreciable self-heating of the sensor cell 20. Typically, the currents are in the order of tens of microamps. The furnace 30 functions to maintain the operating temperature of the sensor cell 20 at a temperature consistent with the temperature of combustion of the fuel constituent of interest, i.e., $H_2$, CO, $CH_4$, etc. Such temperatures are typically in the range of 500° C to 1000° C.

Figure 3:
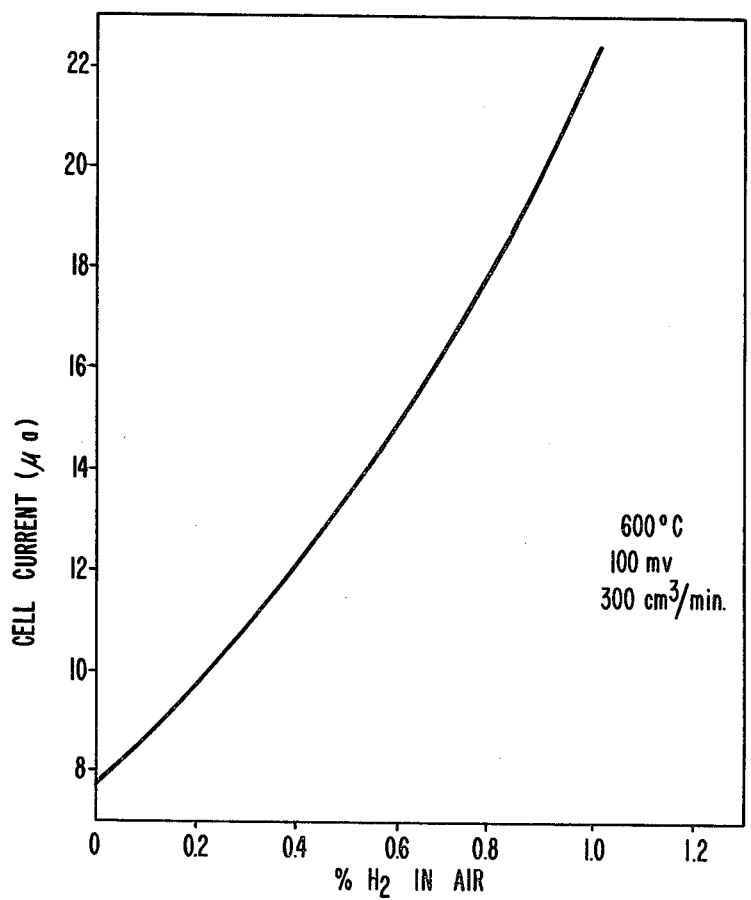
FIG. 3 is a graphical illustration of cell current v. % combustibles response of the solid electrolyte sensor.

The catalytic reactive electrodes 24 and 26 function to catalytically combust the combustibles or fuel with the oxygen present in the monitored gas environment ME and in so doing produce an increase in the temperature of the sensor cell 20. The increase in cell temperature resulting from the combustion of the combustibles at the catalytic electrodes 24 and 26 produces a decrease in the resistance of the thermistor cell 20 and a corresponding increase in the cell current as measured by the ammeter 42. A cell current versus present combustibles response of the sensor cell 20 at an applied DC potential of 100 millivolts and a furnace operating temperature of 600° C of a monitored gas environment including hydrogen ($H_2$) in air is illustrated in FIG. 3

The combustion enthalpy (H) at 25° C for $H_2$, CO and $CH_4$ are defined below:

(a)

$$H_2 + \tfrac{1}{2}O_2 \rightarrow H_2O(g)$$
$$\Delta H = -57.8 \text{ kcal/mol}$$

(b)

$$CO + \tfrac{1}{2}O_2 \rightarrow CO_2$$
$$\Delta H = -67.64 \text{ kcal/mol}$$

(c)

$$CH_4 + 3O_2 \rightarrow CO_2 + 2H_2O$$
$$\Delta H = -191.76 \text{ kcal/mol}$$

The heat produced from equi-molar amounts of combustibles, i.e., same % levels, is quite different between $CH_4$ and the other gases. $CH_4$ will produce a temperature effect which is approximately three times higher than either $H_2$ or CO.

An important consideration in the design of the sensor cell 20 is the heat capacity of the cell. It is essential to maximize the cell surface area and minimize the volume so that heat is not dissipated in the cell volume. Further, heat sink effects of sensor cell mounting must be considered. The potential adverse effects of mounting are eliminated in the embodiment of FIG. 1 wherein the sensor cell 20 is suspended from the lead wires.

The disc or capsule cell design of FIG. 1 further optimizes the surface-to-volume ratio desired for optimum sensor cell operation.

The sensitivity of the combustible sensor 10 can be increased by employing two sensor cells 50 and 52 in a bridge circuit, wherein sensor cell 50 which forms one leg of the bridge circuit is located in the monitored environment ME while the sensor cell 52 is located in an oxygen environment, i.e., air, which is free of combustibles.

Figure 4A:
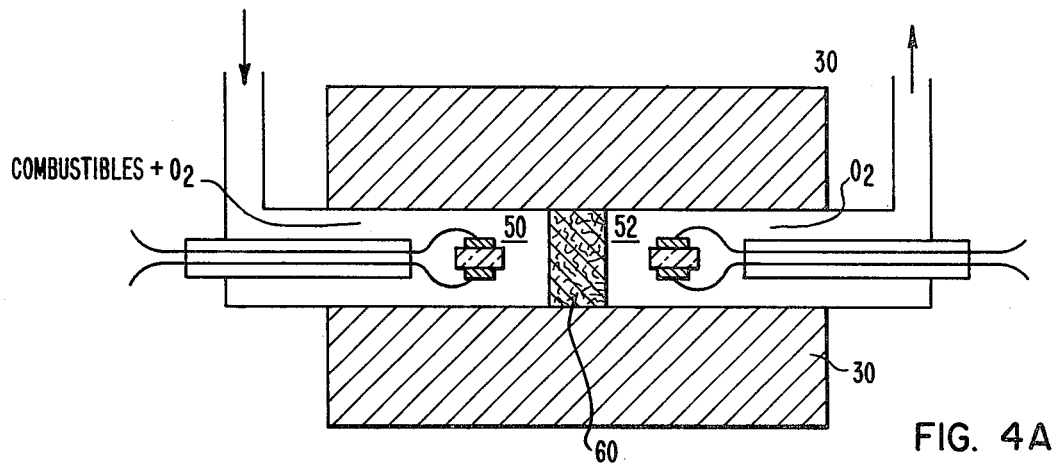
FIGS. 4A and 4B are schematic illustrations of an alternate embodiment of the invention.
Figure 4B:
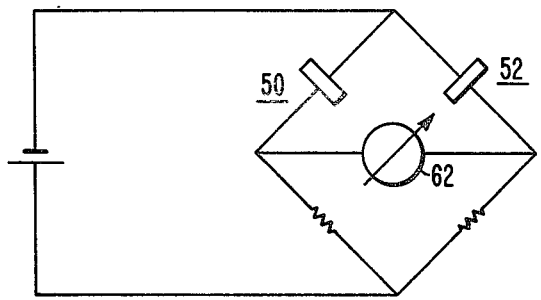

The gas environments present at the sensor cells 50 and 52 can be developed by first flowing the combustibles oxygen monitored gas environment ME in contact with the sensor cell 50 which functions as described above to deplete the combustibles content resulting in a cell resistance change and a corresponding cell current output. Then the combustibles free gas mixture remaining following the catalytic combustion action of the catalytic electrodes of the sensor cell 50 passes through a catalyst bed 60, herein illustrated as consisting of palladium asbestos, to assure removal of any remaining combustibles in the gas prior to contact with the sensor cell 52. Thus the sensor cell 52 is exposed to a combustibles free oxygen containing gas mixture with the sensor cell 52 functioning as a reference cell in the bridge circuit of FIG. 4B. The electrical imbalance of the bridge circuit of FIG. 4B, as monitored by voltmeter 60, is an indication of the combustibles concentration in the combustibles/oxygen monitored gas environment ME introduced to the sensor cell 50. The furnace 64 of the embodiment of FIG. 4A functions to both maintain the sensor cells 50 and 52 at prescribed similar or different operation temperatures and further maintains the temperature of the catalyst bed 60 at a suitable operating temperature.

We claim:

1. A combustible sensor for measuring the concentration of a combustible in an excess oxygen gas environment, comprising a first and a second resistance element, each of said resistance elements being of a material which conducts electrical current at elevated temperatures on the basis of a vacancy mechanism involving doubly charged oxygen ions, said resistance elements having a resistance characteristic which varies exponentially with the inverse of the resistance element temperature, and a pair of electrodes disposed on opposite surfaces of each of said first and second resistance elements, said pair of electrodes associated with said first resistance element being catalytic electrodes, heater means associated with said first and second resistance elements to maintain said resistance elements at desired operating temperatures, said heater means maintaining said first resistance element at a temperature corresponding to the temperature of combustion of the combustibles constituent of interest, said catalytic electrodes combusting said combustibles constituent and the heat of combustion causing an increase in the temperature of said first resistance element and a corresponding decrease in the resistance of said first resistance element, the surface to volume ratio of said first resistance element being such as to minimize dissipation of heat in said first resistance element, and an electrical bridge circuit, said first and second resistance elements each forming one leg of said bridge circuit such that changes in the resistance of said first resistance element in response to said heat of combustion produces an electrical imbalance, the electrical imbalance of said bridge circuit being an indication of the concentration of said combustibles constituent in said gas environment.

2. A combustible sensor as claimed in claim 1 wherein said first and second resistance elements are adapted to be sequentially exposed to the monitored gas environment such that the second resistance element is exposed to a monitored gas environment substantially free of said combustibles constituent, further including a porous catalyst disposed between said first and second resistance elements to assure removal of any combustibles constituent remaining in the gas prior to contact with said second resistance element.

* * * * *